US006939668B2

(12) United States Patent
Keshavje et al.

(10) Patent No.: US 6,939,668 B2
(45) Date of Patent: Sep. 6, 2005

(54) COMPOSITIONS AND METHODS FOR TREATMENT OF LUNG TRANSPLANTS

(75) Inventors: Shaf Keshavje, Toronto (CA); Janet Forstner, Toronto (CA); Umadevi Sajjan, The Hospital for Sick Children Div. of Structural Biology & Biochemistry 555 University Avenue, Toronto, Ontario (CA), M5O 1X8

(73) Assignees: University Health Network, Toronto (CA); Umadevi Sajjan, Toronto (CA)

( * ) Notice: Subject to any disclaimer, the term of this patent is extended or adjusted under 35 U.S.C. 154(b) by 161 days.

(21) Appl. No.: 10/166,319

(22) Filed: May 22, 2002

(65) Prior Publication Data

US 2003/0134773 A1 Jul. 17, 2003

Related U.S. Application Data

(60) Provisional application No. 60/292,321, filed on May 22, 2001.

(51) Int. Cl.$^7$ .......................... A01N 1/00; A01N 43/04; A61F 2/04
(52) U.S. Cl. .......................... 435/1.1; 435/1.2; 514/53; 514/54; 514/59; 600/36
(58) Field of Search .................... 435/1.1, 1.2; 514/53, 514/54, 59; 600/36

(56) References Cited

U.S. PATENT DOCUMENTS

| | | |
|---|---|---|
| 5,441,938 A | 8/1995 | Speert et al. |
| 5,514,665 A | 5/1996 | Speert et al. |
| 5,719,196 A | 2/1998 | Uhari et al. |
| 6,066,677 A | 5/2000 | Uhari et al. |
| 6,143,330 A | 11/2000 | Aaltonen et al. |

OTHER PUBLICATIONS

Struber et al., "Flush Perfusion with Low Potassium Dextran Solution Improves Early Graft Function in Clinical Lung Transplantation", European Journal of Cardio–thoracic Surgery 19 (2) : 190–4 (2001).*
Zabner, J., et al., (2000), The osmolyte xylitol reduces the salt concentration of airway surface liquid and may enhance bacterial killing, PNAS v. 97, pp. 11614–11619.
Kontiokari, T. et al., (1998), Antiadhesive effects of xylitol on otopathogenic bacteria, J. Antimicrobial Chemotherapy, v. 41, pp. 563–565.

Kontiokari, T. et al., (1999), Quantitative analysis of the effect of xylitol on pneumococcal nasal colonisation in rats, FEMS Micro Biol., Lett., v. 178, pp. 313–317.
Uhari, M. et al., (2001), Xylitol in preventing acute otitis media, Vaccine, v. 19, pp. S144–S147.
Klein, J. O., (2000), Nonimmune strategies for prevention of otitis media, Pediatr. Infect. Dis. J., v. 19, pp. S89–S92.
Kontiokari, T. et al., (1995), Effect of Xylitol on Growth of Nasopharyngeal Bacteria In Vitro, Antimicrob. Agents and Chemotherapy, v. 39, pp. 1820–1823.
Moeira et al., (2001), Amer. J. Respir. and Crit Care Med., v. 163, p. A564 (Abstract).
Sajjan, U., et al., (1993), Role of a 22–Kilodalton Pilin Protein in Binding of *Pseudomonas cepacia* to Buccal Epithelial Cells, Infection and Immunity, v.61, pp. 3157–3163.
Sajjan, U., et al., (1992), Identification of the Mucin–Binding Adhesin of *Pseudomonas cepacia* Isolated from Patients with Cystic Fibrosis, Infection and Immunity, v.60, pp. 1434–1440.
Sylvester, F., et al., (1996), *Burkholderia* (Basony *Pseudomonas*) *cepacia* Binding to Lipid Receptors, Infection and Immunity, v.64, pp. 1420–1425.
Sajjan, U., et al., (2000), Cable–Piliated *Burkholderia cepacia* Binds to Cytokeratin 13 of Epithelial Cells, Infection and Immunity, v.68, pp. 1787–1795.
Govan, J., et al., (1996), *Burkholderia cepacia*: medical, taxonomic and ecological issues, J. Med. Microbiol, v.45, pp. 395–407.
Speert, D., et al., (1994), Infection with *Pseudomonas cepacia* in Chronic Granulomatous Disease: Role of Non-oxidative Killing by Neutrophils in Host Defense, Journal of Infectious Diseases, v.170, pp. 1524–1531.
Govan, J., et al., (1996), Microbial Pathogenesis in Cystic Fibrosis: Mucoid *Pseudomonas aeruginosa* and *Burkholderia cepacia*, Microbiological Reviews, v.60, pp. 539–574.
Barghouthi, S., (1996), Inhibition by Dextran of *Pseudomonas aeruginosa* Adherence to Epithelial Cells, Am J Respir Crit Care Med, v.154, pp. 1788–1793.

* cited by examiner

*Primary Examiner*—Sandra E. Saucier (57) ABSTRACT

Methods and compositions for pre-treatment of lung transplants to reduce susceptibility to post-operative *B. cepacia* infection are provided. The methods and compositions employ saccharides, particularly dextrans and xylitol, which are applied to the lung transplant before transplantation.

19 Claims, 4 Drawing Sheets

COMPOSITIONS AND METHODS FOR TREATMENT OF LUNG TRANSPLANTS

RELATED APPLICATION INFORMATION

This application claims the benefit of U.S. Provisional Application No. 60/292,321, filed May 22, 2001, which is incorporated by reference herein in its entirety.

FIELD OF THE INFECTION

The present invention relates to therapies for treating lung pathogen infection in humans, and more particularly, to compositions and methods for pre-treating lung transplants prior to transplantation.

BACKGROUND OF THE INVENTION

Chronic bronchopulmonary infections are the major cause of morbidity and mortality in cystic fibrosis (CF) patients. *Pseudomonas aeruginosa* is the predominant respiratory tract pathogen in patients with cystic fibrosis leading to progressive pulmonary deterioration. Treatments utilizing polysaccharides for the treatment of *P. aeruginosa* infection in CF patients have been suggested but are not yet in general use. In vitro experiments have shown that dextran can inhibit the adherence of *P. aeruginosa* to epithelial cells (Barghouthi et al, Am. J. Respir. Crit. Care Med. 1996, 154:1788–1793) and that xylitol has antimicrobial effects on coagulase negative staphyloccus (Zabner et al., PNAS, 2000, 97:11614–11619). U.S. Pat. No. 5,441,938 is directed to the use of D-glucose or D-mannose in the treatment or prevention by *P. aeruginosa* in cystic fibrosis patients. U.S. Pat. No. 5,514,665 is directed to methods and compositions using the polysaccharides dextran sulfate or dextran for the treatment of *P. aeruginosa* infection in vivo in compromised hosts such as cystic fibrosis patients. Polyols such as xylitol have also been used in methods of treating *S. pneumoniae* respiratory infections as is disclosed in U.S. Pat. Nos. 5,719,196, 6,066,677 and 6,143,330.

Although *Pseudomonas aeruginosa* is the major opportunistic respiratory pathogen isolated from CF patients, a subgroup of these patients (3–5% globally) also becomes infected with *Burkholderia cepacia* which is a particularly infectious bacterial species that is resistant to killing by standard antimicrobial preparations. In North America, the prevalence is about 8–10% and is much higher in the certain clinics such as the Toronto adult CF clinic (46%). The clinical outcome of *B. cepacia*-infected patients is unpredictable and varies widely, from no adverse effects to fatal necrotizing pneumonia within a few months of infection (cepacia syndrome) or after being colonized for several years.

*B. cepacia* is a common soil- and water-borne Gram negative bacterium known to infect not only patients with CF, but also patients with chronic granulomatous disease (CGD) (Govan J. R., Deretic V. Microbiol. Rev. September 1996;60(3):539–74). *B. cepacia* is highly resistant to killing by cationic antimicrobials such as aminoglycosides, polymyxin B, and defensins due to the low levels of negatively-charged phosphate residues in the core region of its outer membrane. This property allows it to readily infect CGD patients, whose neutrophils lack the capacity to generate bacteriocidal oxygen radicals and rely only on non-oxidative cationic-peptide-based bacteriocidal mechanisms (Speert D. P., Bond M, Woodnian R. C., Curnutte T. J. Infectious Diseases. December 1994; 170(6):1524–31). In addition in its resistance to cationic antibiotics, *B. cepacia* is also highly resistant to most other antibiotics (Govan J. R., Hughes J. E., Vandamme P. J Med. Microbiol. December 1996.;45(6):395–407), necessitating the use of near-toxic antibiotic doses for therapy.

*B. cepacia* is a complex organism and has been classified into more than 8 genomovars based on phenotypic and genotypic characteristics. The strains most commonly isolated from CF patients belong to genomovars II, III and IV. *B. cepacia*-colonized patients in eastern Canada and the U.K. carry a highly transmissible strain of genomovar III commonly known as ET12, and this strain has been linked to the fatal cepacia syndrome in CF centers. This strain expresses giant surface pili designated cable pili, and a 22 kDa adhesin protein associated with these pili mediates the adherence of bacteria to airway epithelia and luminal mucus.

Lung transplantation is accepted as a treatment for CF patients with end stage lung disease. Each year, a major proportion of lung transplants performed in large centres such as Toronto are in CF patients. Many transplant centers refuse to perform this procedure on *B. cepacia* infected patients, since the 5-year survival rates of such patients is low compared with survival rates for patients previously colonized by *P. aeruginosa*. Prognosis following transplantation is poor in patients colonized with *B. cepacia* prior to lung transplantation and the one year survival rate is only 61%, which is lower than patients not colonized with this organism (88%). This problem is made worse by the facts that lung transplant recipients are immunosuppressed and *B. cepacia* is intrinsically resistant to multiple antibiotics.

In addition to the problem of *B. cepacia* resistance to antibiotics, it is well recognized that damaged airway epithelium has increased susceptibility to invasive bacterial infection. Thus, after transplantation in CF patients, one is faced with an injured airway epithelium, a pan-resistant, aggressively invasive organism and an immunosuppressed host—all of which translate into significantly increased infectious morbidity and mortality in this group. Although post-transplantation antibiotic strategies have improved the survival rate for *B. cepacia*-infected patients, other strategies are clearly needed to further improve the prognosis and prevent the infection and reinfection of lung allografts by *B. cepacia* and other organisms in transplant patients, including cystic fibrosis patients.

SUMMARY OF THE INVENTION

The present invention is directed to the ex vivo and in vivo use of non-toxic saccharides for the treatment and prevention of *B. cepacia* infection in transplanted lung tissues. Saccharides such as dextran and xylitol may be used to block the initial adherence of *B. cepacia* to donor airway epithelia. Adherence of bacteria to airway mucus and mucosa is the first step of respiratory infection and blocking this step using dextran and/or xylitol is a significant step in preventing infection.

In order to improve the survival of lung transplant recipients, particularly those suffering from CF, lung transplants are treated with dextran, xylitol or a mixture thereof, ex vivo, prior to transplantation.

In accordance with one embodiment, a method of treating a lung transplant prior to transplantation into a recipient to reduce post-operative susceptibility to bacterial infection comprises:

treating a lung transplant, prior to transplantation into a recipient, with an effective amount of a material selected from the group consisting of a sugar, a polysaccharide and a mixture thereof.

In accordance with a further embodiment, a method of treating a patient in need of a lung transplant comprises:

transplanting the patient with a lung transplant treated by the method described above; and administering an effective amount of a material selected from the group consisting of a sugar, a polysaccharide and a mixture thereof to the patient for an effective period of time before and after the transplantation.

In accordance with a further embodiment, a method of treating a lung transplant to reduce adhesion thereto of bacterial pathogens by treating the transplant with a material is selected from the group consisting of a sugar, a polysaccharide and a mixture thereof.

BRIEF DESCRIPTION OF THE DRAWINGS

Certain embodiments of the invention are described, reference being made to the accompanying drawings, wherein.

DETAILED DESCRIPTION OF THE INVENTION

The present invention provides a method of pre-treating a lung transplant prior to transplantation to a recipient to reduce post-operative susceptibility of the transplant to bacterial infection, including infection by *B. cepacia, P. aeruginosa, Staph. aureus* and *Strep. pneumoniae*.

As used herein, "lung transplant" means any lung tissue which is to be transplanted and includes a single lung, a pair of lungs and a combined heart-lung transplant.

In accordance with the invention, a lung transplant is treated with a sugar or a polysaccharide, or a mixture thereof prior to transplantation into a recipient, to reduce adherence of bacteria. This treatment protects the lung transplants against bacterial infection in the early stages after transplantation. For treatment, xylitol or a dextran are preferred. Dextrans in the molecular weight range 1 kDa to 70 kDa are preferred and those of 4 kDa to 40 kDa are especially preferred.

In one aspect, where a lung transplant is to be obtained from a cadaveric donor, the lung transplant is treated by administering a sugar such as xylitol, a polysaccharide such as dextran or a mixture thereof to the transplant prior to removal of the transplant from the donor.

The transplant is treated by administering the xylitol, dextran or mixture to the airways of the cadaveric donor, for example by transtracheal administration of a liquid preparation of the desired compound or by administration of the compound into the lungs in the form of an aerosol.

Lung transplants are also obtained from living adult donors who donate one lung or from people killed by various traumas such as accidents or head injuries. In these cases, the lung transplant is treated with xylitol, dextran or a mixture thereof ex vivo, prior to transplantation, by bathing the transplant in a solution of xylitol and/or by instilling such a solution into the airways of the transplant.

A lung transplant from a cadaveric donor may be treated as described above both before removal from the donor and ex vivo before transplantation.

As an additional protection against post-operative bacterial infection of the transplanted lungs, a lung transplant recipient may receive treatment with a sugar such as xylitol, a polysaccharide such as dextran or a mixture thereof both before and after the transplantation operation. Before transplantation, xylitol, dextran or a mixture thereof is administered either topically or by aerosol inhalation to the nasopharyngeal area of the recipient to reduce any reservoir of bacteria in that area.

Additionally, the recipient may be treated with xylitol, dextran or a mixture thereof for a suitable period of time after transplantation by instillation of a liquid preparation of the desired compound or mixture or administration of an aerosol preparation into the lungs of the recipient. The nasopharyngeal area of the recipient may also be treated as in the pre-operative treatment described above, to reduce the bacterial reservoir in that area.

For treatment of a lung transplant by instillation or aerosol either before removal from a cadaveric donor or after transplantation into a recipient, the xylitol, dextran or mixture may be mixed with any pharmaceutically acceptable diluent or solvent suitable for lung instillation. Sterile saline is preferred.

Concentrations of xylitol or dextran in the range of 6 to 10 gm % are preferred for treatment. One of skill in the art is able to vary these concentrations in light of the response of the patient, where treatment is administered post-operatively to a lung transplant recipient. About 50 ml to about 200 ml of solution containing xylitol, dextran or a mixture may be administered to a lung transplant or to the lungs of a donor or transplant recipient.

Similar preparations of xylitol, dextran or a mixture thereof may be used for ex vivo bathing or instillation of a lung transplant.

Dextran is a polysaccharide having a wide range of molecular weights. It is known as an anti-coagulant, as an anti-lipemic agent and as an anti-ulcer agent.

Xylitol is a monosaccharide, classified as a polyol or sugar alcohol. Both dextran and xylitol are terms recognized by persons skilled in the art.

With the novel demonstration that dextran and xylitol are effective for the inhibition of binding of *B. cepacia* genomovars to respiratory epithelial surfaces, pharmaceutical formulations containing such and novel methods of their use may now be employed against this pathogen. In particular, pharmaceutical formulations containing dextran or xylitol can be prepared in effective concentrations for the prevention and treatment of bacterial infection, including *B. cepa-*

*cia* infection in post-transplant lungs. The pharmaceutical formulations may contain suitable pharmaceutical carriers and excipients well known to those of skill in the art and may be administered as described above.

As an aerosol, the composition may be administered via inhalation through the nose or mouth and thus more directly to the airways of the lung. If it is desired to direct the compositions to buccal, nasal, sinus or respiratory epithelial cells, an aerosol composition administered via the nose (via nasal mist for example) or mouth (via inhaler) may be most effective. The compositions of the present invention may also be administered as a liquid or mist through an endotracheal tube as required, to lung transplant patients after surgery. One skilled in the art would understand that the compositions of the present invention may be provided in a wide variety of formats for in vivo administration. Dosage regimens may vary widely.

The compositions of the present invention also have use in the ex vivo treatment of lung allografts prior to transplantation into a recipient patient. Such compositions may be used to "bathe" the lung allograft tissue for a period of time prior to the tissue being surgically transplanted into the recipient, or by instillation into the lung, as described above. Such methods would be suitable for any type of lung tissue allograft and may help to prevent the colonization of bacteria such as *B. cepacia* in the transplanted tissues. Thereafter, the compositions of the present invention may be administered as required to the transplant recipient to continually prevent or control and ameliorate bacterial infection. In a preferred embodiment, administration of the dextran, xylitol or mixed compositions of the invention is continued throughout the first three months after the transplantation surgery. This is a critical time period in which the patient is severely immuno-compromised and susceptible to bacterial infection, including *B. cepacia* infection.

*B. cepacia* is a particularly infectious and difficult to treat organism. Thus the effectiveness of these non-toxic saccharides against *B. cepacia* is quite remarkable and unexpected.

The in vitro model system used to study bacterial adherence, as described in the examples herein, closely resembles the in vivo situation with well-differentiated respiratory epithelia containing mucus secreting and ciliated cells, and a protective coat of mucus covering apical surface of the epithelia. This is particularly relevant in patients with septic lung diseases (such as CF) who are treated by lung transplantation. All species of *B. cepacia* exhibited binding to airway explants and this binding occurred due to entrapment of bacteria in the mucus layer. Dextran and xylitol significantly reduced the number of bound bacteria. Both agents also reduced the thickness of the mucus layer.

Although lung transplantation is currently the only treatment for CF patients with end stage lung disease, it is associated with high risks in patients that are colonized with pan-resistant bacterial organisms. CF patients who undergo bilateral lung transplantation typically become re-infected with their original strains of bacteria within the first days to weeks after the operation. The immunosuppression that is required to prevent rejection of the transplant creates a favorable environment and a more vulnerable host, especially for organisms such as *B. cepacia*.

Adherence of bacteria to the host airway mucosal surface is an important initial event in infection. Dextran and xylitol do not appear to interfere with specific adhesin-receptor interactions. In *B. cepacia*, these include mucin glycoproteins, cytokeratin 13 and glycolipids such as asialo GM1 and Gg4 (Sajjan et al., (2000), Infect. Immun., v. 68, pp. 1787–1795; Sajjan et al., (1991), supra; Sylvester et al., (1996), Infect. Immun., v. 64, pp. 1420–1425). The bacterial adhesin, which mediates binding to cytokeratin 13 and mucin glycoproteins, has been identified as a 22 kDa protein associated with cable pili (Sajjan et al., (1992), Infect. Immun., v. 60, pp. 1434–1440; Sajjan et al., (1993), Infect. Immun., v. 61, pp. 3157–3163) and the adhesin that mediates binding to glycolipids is yet to be identified. The 22 kDa adhesin is expressed only by a highly transmissible ET12 strain of genomovar III, which is the most common and highly virulent strain recovered from CF patients at the Toronto center. The observed binding of *B. cepacia* to explants is probably not via the adhesion but is by entrapment in adherent mucus gel on surface. Evidence for this lies in the observation that all species of *B. cepacia*, irrespective of expression of cable pili-associated 22 kDa adhesion, demonstrated almost equal binding. Secondly, both dextran and xylitol were found to reduce the surface mucus layer, suggesting that the decreased binding of bacteria in the presence of these agents is likely due to removal of the mucus layer along with the trapped bacteria.

It has been shown that neutral polysaccarides such as dextran, mannan and glycogen can efficiently inhibit the adherence of respiratory pathogens to alveolar epithelial cells. It has been suggested that this inhibition is largely due to a non-specific mechanism because these large polysaccharides interfere with binding mainly by coating bacterial or host cell surfaces, thus masking cell surface receptors. Dextrans in the 4 to 10 kDa range have been shown to be more effective than the higher molecular weight dextrans in inhibiting binding of *P. aeruginosa* and isolates of *B. cepacia* complex including ET12 strains to alveolar pneumocytes. In the present study, however, low molecular weight dextrans did not inhibit the binding of *B. cepacia* ET12 strain effectively to tracheal explants. The tracheal explant model described herein showed well-differentiated respiratory epithelium with adherent surface mucus and hence is more relevant to the in vivo situation than alveolar pneumocytes. The inventors' findings suggest that bound *B. cepacia* remained in the apical mucus layer and did not reach the cellular surface or enter cells even after 24 h. Thus efficient removal of mucus, with entrapped bacteria, by dextrans or xylitol may be used to prevent or reduce bacterial invasion and infection of lung transplants and to improve the post-operative survival of lung transplants free of infection by organisms such as *B. cepacia*.

EXAMPLES

The examples are described for the purposes of illustration and are not intended to limit the scope of the invention.

Methods of biochemistry, histology, immunology and cell culture referred to but not explicitly described in this disclosure and examples are reported in the scientific literature and are well known to those skilled in the art.

Example 1
Maintenance of Tracheal Explants in Culture

Sections of normal trachea from donors were obtained at the time of lung transplantation, stored in RPMI 40 medium containing pen/strep and fungizone, and transported to the lab. Pieces of 4×4 mm were cut from undamaged areas of the trachea and placed in transwells with the epithelium facing up. The tracheal explants were maintained at 37° C., 95% $O_2$/5% $CO_2$ in bronchial epithelial cell growth medium (Clonetics, San Diego) at an air/liquid interface.

Tracheal explants maintained at an air/liquid interface retain normal morphology up to about 24 hours.

Bacterial Adherence Assay

*B. cepacia* ($10^7$–$10^8$ cfu) in 5 µl was added to the epithelial surface of tracheal explants, incubated for 2 h at 37° C. and gently washed with PBS 5 times to remove unbound bacteria.

Bound bacteria were desorbed with 0.25% triton X-100, serially diluted and plated on *B. cepacia* isolation agar, and incubated at 37° C. for 72 hours. Colonies were counted to calculate the number of bacteria bound per explant. When inhibitors were used, explants were incubated with inhibitors for 1 hour prior to the addition of bacteria.

Microscopy

Scanning, transmission and light microscopy were performed by conventional techniques. Immunolocalization was carried out using anti-*B. cepacia* antiserum followed by second antibody conjugated to Cy3.

Immunolocalization of *B. cepacia* Isolate BC7 in Tracheal Explants Incubated in the Presence or Absence of Dextran 40K Tracheal explants were incubated with *B. cepacia* isolate BC7 ($10^7$ cfu) for 2 hours in the presence or absence of dextran 40K. Explants were washed with PBS, fixed in buffered formalin, and embedded in paraffin. Section (5 µm thick) were deparaffinized and incubated with anti-*B. cepacia* antibody. Bound antibody was detected by anti-rabbit IgG conjugated with CY3 fluorophore and was all located in the surface mucus layer.

Figure 1:
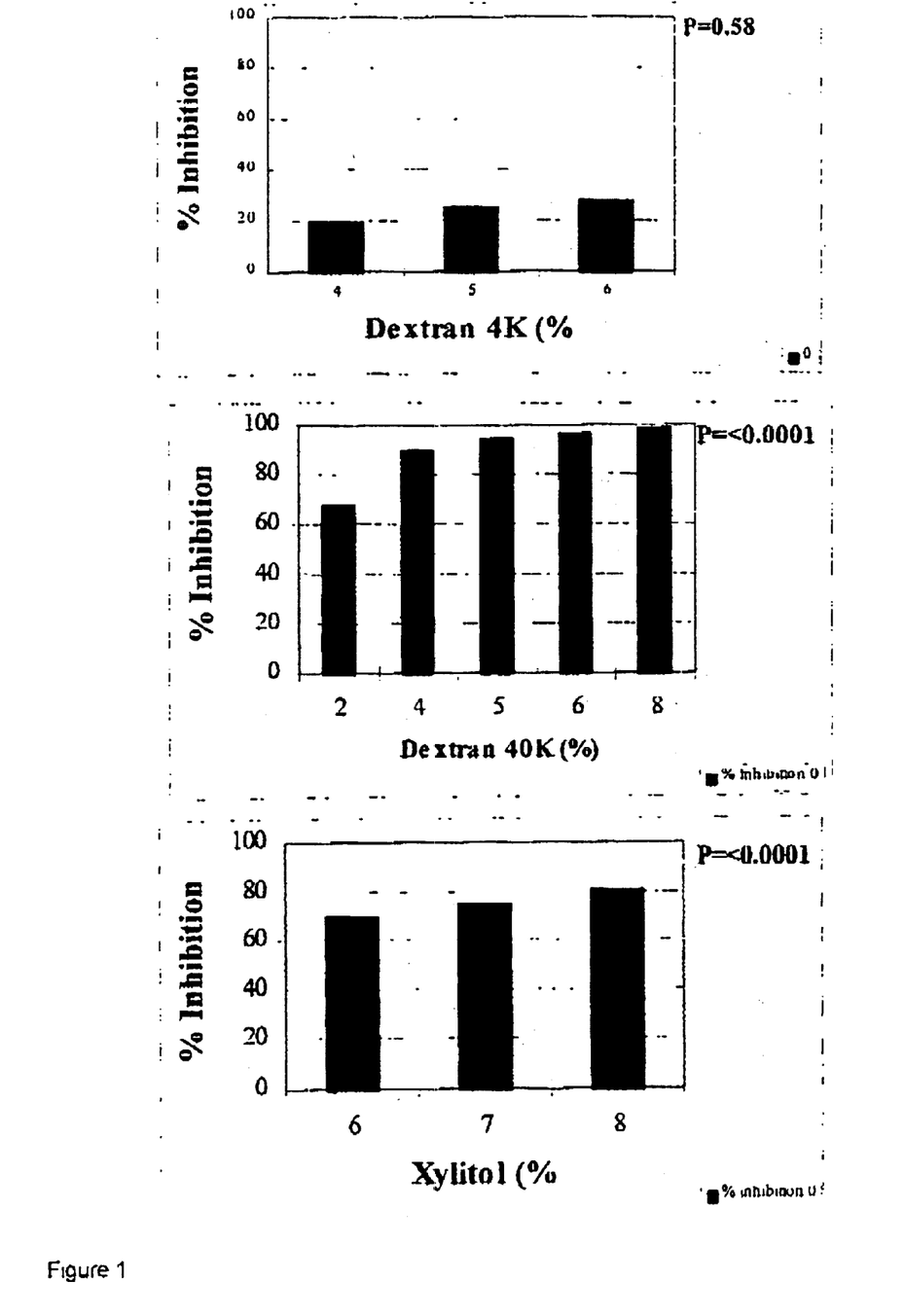
FIG. 1 shows the inhibition of *B. cepacia* BC7 binding (% inhibition) to tracheal explants by dextran 4K, dextran 40K and xylitol.

Inhibition of *B. cepacia* BC7 Binding to Tracheal Explants by Dextran 4K, Dextran 40K and Xylitol Tracheal explants were preincubated for 1 hour with dextran 4K or 40K or xylitol. Bacteria ($10^7$ or $10^8$ cfu) were then incubated for 2 hours with the tracheal explants and the number of bound bacteria per explant was determined as described above. Results are shown in FIG. 1 and Table 1. Bacterial binding to explants preincubated with culture medium alone was considered as 0% inhibition (FIG. 1, each bar represents the mean of 14 to 17 independent experiments using trachea from 5 to 6 donors. Data were analyzed by the mixed model analysis of variance using MIXED procedure in SAS statistical software). Both dextran 40K and xylitol were effective in causing inhibition of bacterial binding, and the observed effects were statistically significant with the p value <0.0001.

Example 2

Materials and Methods

*B. cepacia* strains and culture conditions: All *B. cepacia* isolates except for ATCC 25416 used in this study were isolated from the sputa of CF patients. BC7 and BC45 (genomovar III) were from Toronto CF patients and have been described previously (Sajjan et al. (2000), J. Med. Micro., v. 49 pp. 875–885; Sajjan et al. (1991), J. Clin. Invest., v. 89, pp. 648–656). C5393 (genomovar II), LMG14294 (genomovar IV) and PC259 (genomovar V) are *B. cepacia* research panel isolates (Mahenthiralingam et al. (2000), J. Clin. Microbiol., v. 38, pp. 910–913). ATCC 25416 (genomovar I) is an environmental strain and was purchased from the American Type Tissue Culture Collection, Rockville, Madison. All strains were maintained as glycerol stocks at −70° C. For the binding assays, *B. cepacia* strains were grown on Brain heart infusion agar (Becton Dickinson, Cockeysville, Md., USA) for 48 h at 37° C. A single colony was inoculated into ten ml of Tryptic soy broth (TSB) and grown at 37° C. for 18 h on an orbital shaker at 150 rpm. Bacteria were harvested by centrifugation at 3,000 g for 5 min, the bacterial pellet was washed three times with PBS and then suspended to a final concentration of 2–5×$10^{10}$ cfu/ml.

Sugars: Dextrans of molecular weights 4,000, 10,000 and 40,000 were synthesized and provided by Dextran Products Ltd., Scarborough, Ontario, Canada. Xylitol was purchased from Sigma Chemical Co, St Louis, Mo. Dextrans and xylitol were dissolved in bronchial epithelial cell growth medium (Clonetics, San Diego, Calif.) (BEGM) to a desired concentration, filter sterilized and used in binding assays.

Antibodies: A rabbit polyclonal antibody to *B. cepacia* (R418) has been described previously (Sajjan et al. (2001), J. Med. Microbiol., v. 50, pp. 535–546). Antibody to tracheobronchial mucin was prepared in New Zealand rabbits using purified tracheobronchial mucin as an antigen (Sajjan (1991), supra).

Western blot analysis: Blots of purified tracheobronchial mucins, sputum from cystic fibrosis patients, fibronectin or bovine serum albumin were incubated with 1:10,000 (v/v) antibody to tracheobronchial mucin. Bound antibody was detected by using anti-rabbit IgG conjugated to alkaline phosphatase and colour substrate NBT-BCIP (Roche Molecular Biochemicals, Laval, QC, Canada).

Airway Explants:

Explants were obtained from lungs removed from donors for transplantation. All lungs were preserved using LPD lung preservation solution (Perfadex®, Vitrolife, Gotenberg, Sweden) (Fischer et al. (2001), J. Thorac. Cardiovasc. Surg., v. 121, pp. 594–596). Segments of donor trachea that were trimmed off the lung before implantation were used in this study. Airway explants were prepared from donor tracheal segments, which were cut into approximately 4×4 mm² pieces, placed in transwells with the epithelial surface facing up and maintained in BEGM at an air/liquid interface for a maximum of 24 h at 37° C., 5% $CO_2$. To evaluate the morphological status of the airway explants at this time, the explants were fixed in 10% buffered formalin and embedded in agar-paraffin. Five micron thick sections were stained with hematoxylin and eosin and examined under a light microscope (Leica, Scarborough, ON).

Effect of dextrans and xylitol on the viability of *B. cepacia*: *B. cepacia* ($10^7$ cfu) was suspended in BEGM containing 0, 2, 4, 6, 7 or 8% of dextran or xylitol for 2 h and then the number of viable bacteria was determined by colony counting method.

Binding of *B. cepacia* to airway explants: *B. cepacia* suspended in PBS (5 µl containing $10^8$ cfu) was added in the center of the epithelial surface of airway explants and incubated for 2 h at 37° C., 5% $CO_2$. The explants were washed gently 6 times with sterile PBS to remove unbound bacteria, and bound bacteria desorbed by incubating in 1 ml of 0.25% triton X-100 for 10 min at RT. Samples were serially diluted, and plated on *B. cepacia* isolation agar (Henry et al. (1997), J. Clin. Microbiol., v. 35, pp. 614–619). After 72 h of incubation at 37° C., bacterial colonies were counted to determine the number of bacteria (cfu) bound per explant.

In inhibition assays, epithelia of airway explants were pre-incubated with varying concentrations of potential inhibitors, dextran (4, 10 or 40 kDa) or xylitol for 1 h at 37° C., then bacteria were added and the assay continued as described above. Controls (no inhibitor added) in each experiment were set to a value of 100% binding, to calculate the % inhibition caused by inhibitors. Statistical analysis was carried out using Statsview and the unpaired student's t-test was used to calculate the p value.

Immunological detection of bound bacteria or mucin in airway explants: Paraffin sections of airway explants incubated with PBS or *B. cepacia* in presence or absence of inhibitors were deparaffinized, rehydrated and heated under pressure for 1.5 min in 10 mM citrate buffer pH 6.0 (Shi et al. (1991), J. Histochem. Cytochem., v. 39, pp. 741–748) to retrieve antigenic sites. Sections were rinsed with water, equilibrated in TBS (10 mM tris-HCl buffer pH 7.4 containing 150 mM sodium chloride), blocked with 5% goat serum in TBS for 1 h at RT, and then incubated for 1 h with the anti-*B. cepacia* antibody (R418) (1:1000 dilution) (16) or antibody to tracheobronchial mucins (1:1000). Unbound antibody was removed by washing with TBS three times (10 min each) and sections were then incubated with antirabbit IgG conjugated to CY3 flurophore. Slides were washed 3 times with TBS as before, counter stained with Mayer's hematoxylin and examined under a fluorescence microscope (Leica, Scarborough, ON).

Scanning and Transmission electron microscopy: Airway explants before or after incubation with *B. cepacia* were fixed in universal fixative for 1 h, washed with 0.1 M phosphate buffer (pH 7.4), and incubated in 1% osmium tetroxide in PBS for 1 h. Explants were washed with phosphate buffer, followed by water, and dehydrated in graded alcohol series. For scanning electron microscopy, samples were critical point dried and mounted on carbon coated stubs. The samples were then sputter coated with gold and observed under a JEOL JSM 820 scanning electron microscope (JEOL USA Inc., Peabody, Mass.). For transmission electron microscopy, samples were embedded in epon resin, ultra thin sections (80 nm) were taken and stained with uranyl acetate and observed under JEOL 1200 EXII transmission electron microscope (JOEL USA Inc., Peabody, Mass.)

Statistical analysis: A mixed model variance was conducted to estimate the size and significance of the effects of inhibitors on binding. The mixed model provides robust estimates, accounting for correlated measures originating from the same experimental unit (i.e. explant). The model was calculated with inhibitor (xylitol or dextran) as a continuous variable. The MIXED procedure in SAS statistical software was used to compute the model.

Morphology of airway explants and immunostaining of mucins: Airway explants maintained in BEGM at an air/liquid interface for 24 h showed normal pseudostratified epithelium composed of columnar ciliated cells, goblet cells and a layer of basal cells. The apical surface of the epithelium was covered with a mucus layer. A thick basement membrane, characteristic of proximal airways, was observed following the epithelium. Beneath the basement membrane was the lamina propria with richly vascularized connective tissue (data not shown).

Mucin glycoproteins in the airway explants were detected by immunofluorescence using a polyclonal antibody specific to tracheobronchial mucin. This antibody reacted strongly with purified tracheobronchial mucins and with high molecular weight proteins (>200 kDa) of sputum, but not with either bovine serum albumin or fibronectin on a western blot (data not shown). As expected, in tracheal explants, mucin glycoproteins were detected only on the apical surface of epithelium and in the goblet cells, suggesting that maintaining airway explants in culture for 24 h did not have any effect on the normal distribution of mucin glycoproteins (data not shown).

Binding of *B. cepacia* isolate BC7 to airway explants: *B. cepacia* isolate BC7 exhibited strong binding to airway explants. Consistently 30–40% (3 to $4 \times 10^7$ cfu) of the added bacteria bound to airway explants within 2 h, as determined by the colony counting method on 8 airway explants in triplicate. Control explants incubated with sterile PBS had no recoverable bacteria.

Figure 2:
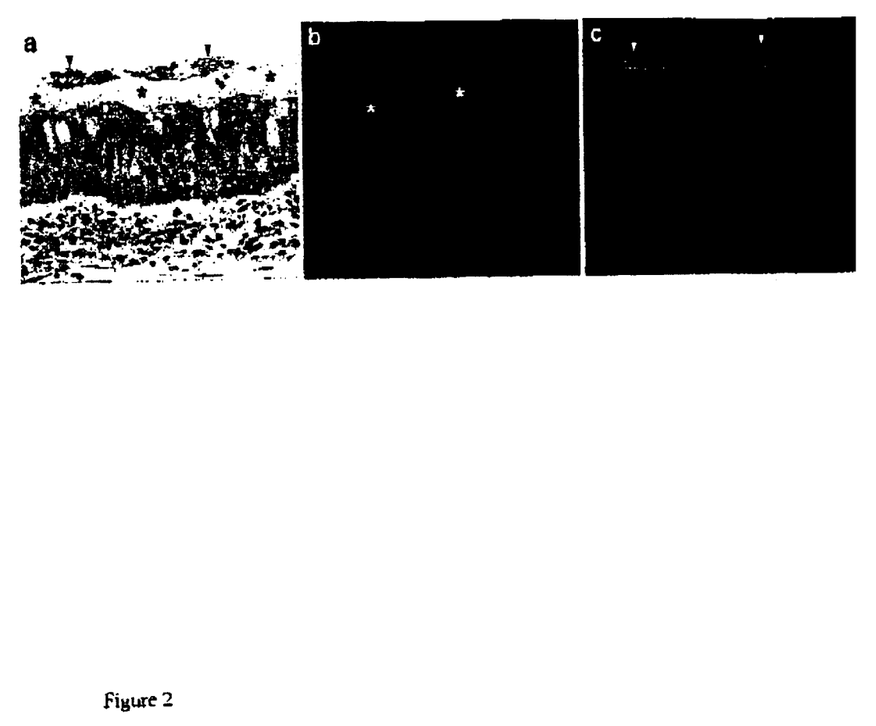
FIG. 2 shows immunolocalisation of bound *B. cepacia* to tracheobronchial mucin: Panel a: H & E staining; Panel b: section treated with antibody to tracheobronchial mucins; and Panel c: section treated with anti-*B. cepacia* antibody R418. Asterisks represent mucin glycoproteins and arrows represent bound bacteria.

Histological evaluation of the airway explants incubated with *B. cepacia* did not show any evidence of morphological changes (FIG. 2a). In order to detect the location of bound bacteria, serial sections of paraffin embedded explants were immunostained with either anti-*B. cepacia* antibody (FIG. 2b) or antibody to tracheobronchial mucin (FIG. 2c). Results revealed that the bound bacteria were mainly in the mucus-like material on the surface of the epithelium, which strongly reacted with the antibody to tracheobronchial mucin, indicating that the bound bacteria were concentrated within the surface mucus layer. Occasionally bacteria were seen in close association with the underlying epithelial cells.

Figure 3:
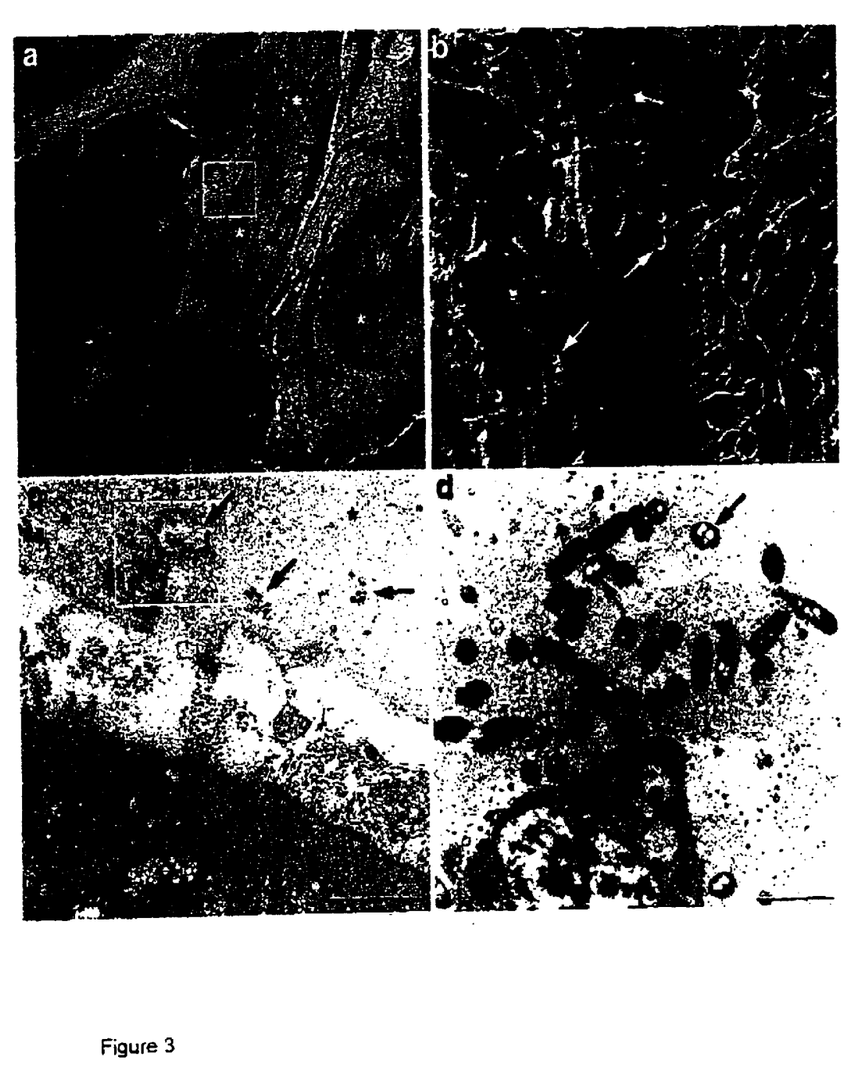
FIG. 3 shows electron micrographs of airway explants incubated with *B. cepacia*. Panel (a): scanning electron micrograph showing surface of the epithelia covered in mucus (asterisk); Panel (b): a magnified view of area marked by the square in panel (a) demonstrating the *B. cepacia* (arrows); Panel (c): transmission electron micrograph showing bacteria in the mucus layer (asterisk=mucus layer, arrows point to bacteria in the mucus layer); and Panel (d): magnified view of area in the square in panel (c) showing bacteria entrapped in the mucus (arrows).

To examine the distribution of bacteria more precisely, airway explants were subjected to scanning and transmission electron microscopy. Scanning EM performed on five different explants, revealed bound bacteria only in the areas where mucus—like material was present (FIGS. 3a and 3b). Bacteria were absent in the areas devoid of mucus and on ciliated cells that had no mucus coating. Transmission EM further confirmed that bound bacteria were confined to mucus layer but were not on the cilia or the plasma membrane of intact cells (FIGS. 3c and 3d). Invasion of normal respiratory epithelia by bacteria was not observed even after 24 h incubation of explants with *B. cepacia* isolate BC7 (data not shown).

Figure 4:
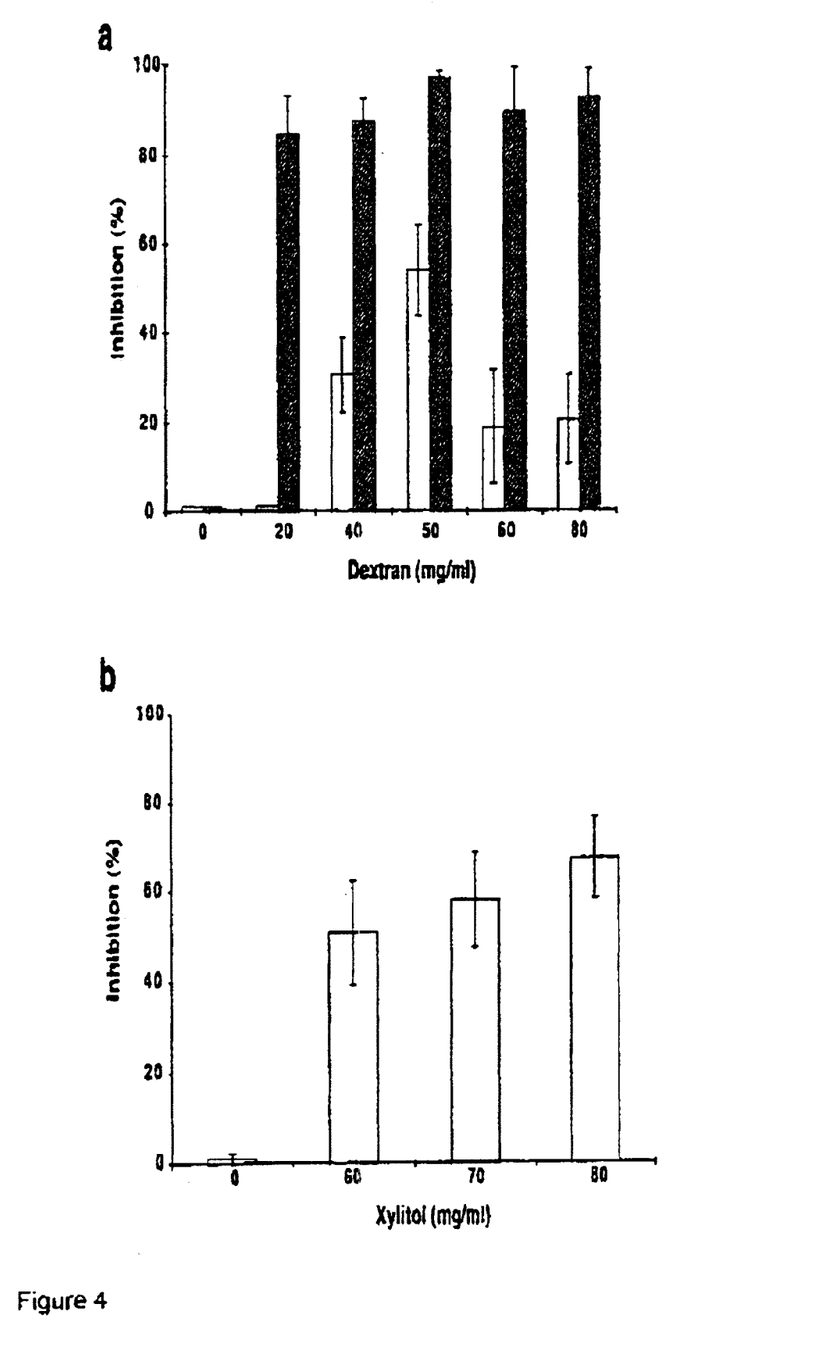
FIG. 4 shows % inhibition of *B. cepacia* binding to airway explants by various concentrations of dextran 4 kDa (Panel a, open bars), dextran 40 kDa (Panel a, hatched bars) and xylitol (Panel b).

Inhibition of *B. cepacia* isolate BC7 binding to airway explants by dextran and xylitol: Dextrans with molecular mass of 4, 10, or 40 kDa, and xylitol were examined for their effect on *B. cepacia* binding to airway explants. Explants were first bathed with varying concentrations of dextran or xylitol and then bacteria were added to the epithelial surface and the number of bacteria bound per explant was estimated after 2 h. Dextran 40 kDa inhibited the binding of *B. cepacia* isolate BC7 effectively (85%) at a concentration as low as 20 mg/ml. This inhibition increased with increasing concentration, reaching 97% at 50 mg/ml (FIG. 4a, hatched bars). Increasing the concentration beyond 50 mg and increase in concentration beyond. The observed inhibitory effect was statistically different from controls (no dextran) at concentrations 40 mg/ml and above with a p value of <0.005. Dextran 4 kDa, on the other hand, inhibited binding to a maximum of 50% at 50 mg/ml (FIG. 4a, open bars) and the effect was not statistically significant. Concentrations above 50 mg/ml did not improve the inhibitory effect. Inhibition pattern exhibited by dextran 10 kDa was very similar to dextran 4 kDa (data not shown).

Xylitol, a polyol, also significantly inhibited the binding of BC7 to airway explants (p<0.005) at concentrations 60 to 80 mg/ml compared to PBS treated controls (FIG. 4b). A higher concentration of xylitol than dextran 40 kDa (80 mg/ml vs. 20 mg/ml respectively) was required, however, even to inhibit the binding by 67%. Although concentrations below 60 mg/ml inhibited the binding, the effect was not statistically significant (data not shown).

To examine whether the reduced binding of *B. cepacia* to airway explants caused by xylitol or dextran occurred as a result of decreased viability, the effect of xylitol and dextran on bacterial viability was determined. In addition, total bound bacteria to airway explants that were pre-incubated with dextran or xylitol was determined by immunofluorescence. *B. cepacia* incubated with xylitol (60 to 80 mg/ml) or dextran 40 kDa (20 to 60 mg/ml) for 2 h showed no change in viability compared to *B. cepacia* incubated with BEGM alone (data not shown).

Microscopic examination of airway explants treated with of dextran 40 kDa (40 mg/ml) did not reveal any morphological changes except for a reduction in the thickness of the mucus layer on the surface of the epithelium as determined by immunofluroescence, using an antibody to tracheobronchial mucin (data not shown). Immunolocalization of bacteria bound to explants pretreated with dextran 40 kDa (40 mg/ml) revealed a few bacterial aggregates on the surface of the airway epithelium. Again the bacteria were observed mainly in association with mucus like material. Airway explants treated with xylitol showed similar results to those treated with dextran 40 kDa (data not shown). Taken together, these results suggest that both dextran 40 kDa and xylitol reduced the number of bound bacteria, rather than decreasing the viability of the bacteria bound to airway explants. In addition, both these agents reduced the surface mucus layer. Since bound B. cepacia were found mainly in the mucus layer in the absence of inhibitors, it is likely that both xylitol and dextran reduced the bacterial binding by removing the surface mucus along with bound bacteria.

Effect of dextran and xylitol on the binding of B. cepacia belonging to other genomovars: Extensive studies carried out with B. cepacia isolate BC7 suggested that dextran 40 kDa and xylitol were effective inhibitors of binding. Hence, we tested the effect of these two agents on the binding of other representative strains of B. cepacia complex to tracheal explants. Binding of representative isolates of genomovars I, II, IV and V to airway explants were initially determined. All four isolates showed binding to normal airway explants as determined by triplicate experiments using at least two different explants. On average, 10 to 30% (1 to $3 \times 10^7$ cfu) of the added bacteria bound to normal airway explants, which is slightly lower than the binding of B. cepacia isolate, BC7. To detect the location of bound bacteria, we subjected the airway explants incubated with isolates of genomovars I, II, IV or V to scanning electron microscopy. As observed earlier with B. cepacia isolate, BC7, bacteria were again observed only in the mucus-like material. The effect of dextran and xylitol on the binding of these B. cepacia isolates was then examined at selected concentrations chosen on the basis of results obtained with BC7. As shown in Tables 1 and 2, both dextran 40 kDa (40 mg/ml) and xylitol (70 mg/ml) inhibited the binding of all four strains, although in most cases dextran was somewhat more efficient.

Example 3

Normal human bronchial epithelial (NHBE) cells were grown in 48 well plates. B. cepacia (0.5 ml containing $10^7$ cfu) either suspended in PBS or PBS containing xylitol (6 to 10%) was added, incubated for 2 h at 37° C. Unbound bacteria were removed by washing 6 times with PBS and the bound bacteria were desorbed in 1 ml of 0.5% triton X-100 and quantitated by dilution plating. Results are shown in Table 3 and represent the mean of 4 independent experiments and the values in parenthesis represent the range of experimental values.

Galactose (0 to 1.8%/ml), glucose (0 to 1.8%/ml), chitobiose (0–100 µg/ml), chitotetraose (0–100 µg/ml), chitopentose (0–100 µg/ml), and chitohexose (0–100 µg/ml) were also tested for their inhibitory effect. None of these sugars inhibited the binding of B. cepacia to NHBE cells.

Although preferred embodiments of the invention have been described herein in detail, it will be understood by those skilled in the art that variations may be made thereto without departing from the spirit of the invention.

TABLE 1

Inhibition of binding of B. cepacia genomovars to tracheal explants by dextran 4K, 40K and xylitol

| | | | | Percent Inhibition | | | | | |
| | | | | Dextran 4K | | Dextran 40K | | Xylitol | |
| Isolates | Genomovar | Source | Cbl pili | 4% | 5% | 4% | 5% | 7% | 8% |
| --- | --- | --- | --- | --- | --- | --- | --- | --- | --- |
| ATCC 25416 | I | Envir. | − | 76 | 76 | 90 | 70 | 82 | 84 |
| C5393 | II | CF | − | 67 | 64 | 85 | 65 | 70 | 68 |
| BC7 | III | CF | + | 36 | 50 | 90 | 98 | 76 | 81 |
| FC473 | IV | CF | − | 58 | 64 | 85 | 82 | 72 | 70 |
| CEP040 | V | CF | − | 89 | 92 | 70 | 70 | 70 | 64 |

TABLE 2

Inhibition of B. cepacia isolates binding to tracheal epithelial cells by Dextran 40 kDa and xylitol

| | | % Inhibition | |
| | | Dextran 40 kDa | Xylitol |
| Isolates | Genomovar | 40 (mg/ml) | 70 (mg/ml) |
| --- | --- | --- | --- |
| ATCC 25416 | I | 90 ± 1.47 | 82 ± 1.29 |
| C5393 | II | 80 ± 4.45 | 70 ± 6.78 |
| BC7 | III | 88 ± 1.25 | 58 ± 10.67 |
| FC473 | IV | 85 ± 4.1 | 70 ± 3.26 |
| CEP040 | V | 90 ± 1.98 | 70 ± 6.75 |

TABLE 3

Effect of Xylitol on B. cepacia binding to normal human bronchial epithelial cells

| Xylitol (%) | % Binding of control | % Inhibition |
| --- | --- | --- |
| None | 100 | 0 |
| 6% | 64 (29–105) | 36 (0–71) |
| 7% | 56 (54–58) | 44 (42–44) |
| 8% | 33 (23–43) | 67 (57–77) |
| 10% | 23 (18–29) | 77 (71–82) |

We claim:

1. A method of treating a lung transplant prior to transplantation into a recipient to reduce post-operative susceptibility to bacterial infection comprising treating a lung transplant, prior to transplantation into a recipient, by transtracheal administration of an effective amount of a material selected from the group consisting of a sugar, a polysaccharide and a mixture thereof.

2. The method of claim 1 wherein the lung transplant is obtained from a cadaveric donor and wherein an effective amount of a material selected from the group consisting of a sugar, a polysaccharide and a mixture thereof is administered to the lung transplant prior to removal of the transplant from the donor.

3. The method of claim 1 wherein the material is selected from the group consisting of xylitol, dextran and a mixture thereof.

4. The method of claim 1 wherein the dextran has a molecular weight in the range of about 1 kDa to about 70 kDa.

5. The method of claim 1 wherein the transplant is treated prior to transplantation into a recipient suffering from cystic fibrosis.

6. The method of claim 1 wherein the bacterial infection is a *B. cepacia* infection.

7. A method of treating a patient in need of a lung transplant comprising:

transplanting the patient with a lung transplant treated by the method of claim 1;

and administering an effective amount of a material selected from the group consisting of a sugar, a polysaccharide and a mixture thereof to the patient for an effective period of time before and after the transplantation.

8. The method of claim 7 wherein the material is administered to the nasopharyngeal area of the patient before and after the transplantation and is administered transtracheally to the lungs of the patient after transplantation.

9. The method of claim 8 wherein the material is selected from the group consisting of xylitol, dextran and a mixture thereof.

10. The method of claim 9 wherein the dextran has a molecular weight in the range of about 1 kDa to about 70 kDa.

11. The method claim 8 wherein of the patient is suffering from cystic fibrosis.

12. A method of treating a lung transplant to reduce adhesion thereto of bacterial pathogens by treating the airways of the transplant with a material selected from the group consisting of a sugar, a polysaccharide and a mixture thereof.

13. The method of claim 12 wherein the material is selected from the group consisting of xylitol, a dextran and a mixture thereof.

14. The method of claim 13 wherein the dextran has a molecular weight in the range of about 1 kDa to about 70 kDa.

15. The method of claim 13 wherein the material is a sugar.

16. The method of claim 15 wherein the sugar is xylitol.

17. The method of claim 13 wherein the material is a polysaccharide.

18. The method of claim 17 wherein the polysaccharide is a dextran.

19. The method claim 12 wherein the pathogen is *B. cepacia.*

* * * * *